Figure 1:
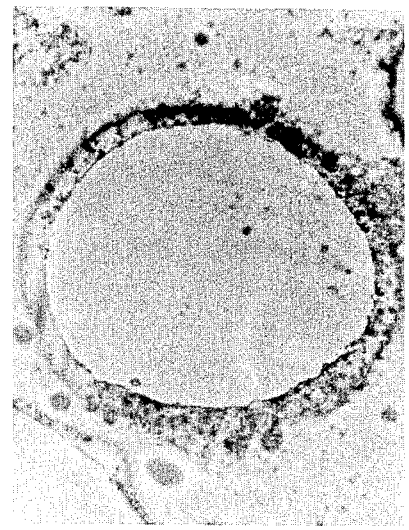

United States Patent [19]

Watanabe et al.

[11] 4,127,622
[45] Nov. 28, 1978

[54] PROCESS FOR THE PREPARATION OF HOLLOW PARTICULATES

[75] Inventors: Sumio Watanabe; Yasuhiko Mizuno; Masanori Kayano, all of Honjo; Yoshio Ishino, Kumagaya, all of Japan

[73] Assignee: Eisai Co., Ltd., Tokyo, Japan

[21] Appl. No.: 615,086

[22] Filed: Sep. 19, 1975

[30] Foreign Application Priority Data

Sep. 19, 1974 [JP] Japan .............................. 49-107111

[51] Int. Cl.² ............................................. B01J 2/02
[52] U.S. Cl. .................................................... 264/13
[58] Field of Search ................................ 264/13, 7, 4

[56] References Cited

U.S. PATENT DOCUMENTS 3,080,293  3/1963  Koff ..................................... 264/13
3,341,415  9/1967  Scott ..................................... 264/13
3,499,962  3/1970  Wurzburg ............................... 264/7
3,888,957  6/1975  Netting .................................. 264/13

Primary Examiner—Robert F. White
Assistant Examiner—James R. Hall
Attorney, Agent, or Firm—Wenderoth, Lind & Ponack

[57] ABSTRACT

A hollow particulate for gastric medicines and other durable medicines suspendable in the gastric juice and remainable in the stomach for a long period of time is provided which has been prepared by dissolving ethylcellulose in a lower chlorinated hydrocarbon, or a mixed solution of the lower chlorinated hydrocarbon and a lower chlorofluorinated hydrocarbon and/or water, so that the concentration of ethylcellulose is 0.5 - 4% by weight on the basis of the total weight of the resulting solution, and then spray-drying the solution at an inlet temperature of higher than 50° C.

17 Claims, 6 Drawing Figures

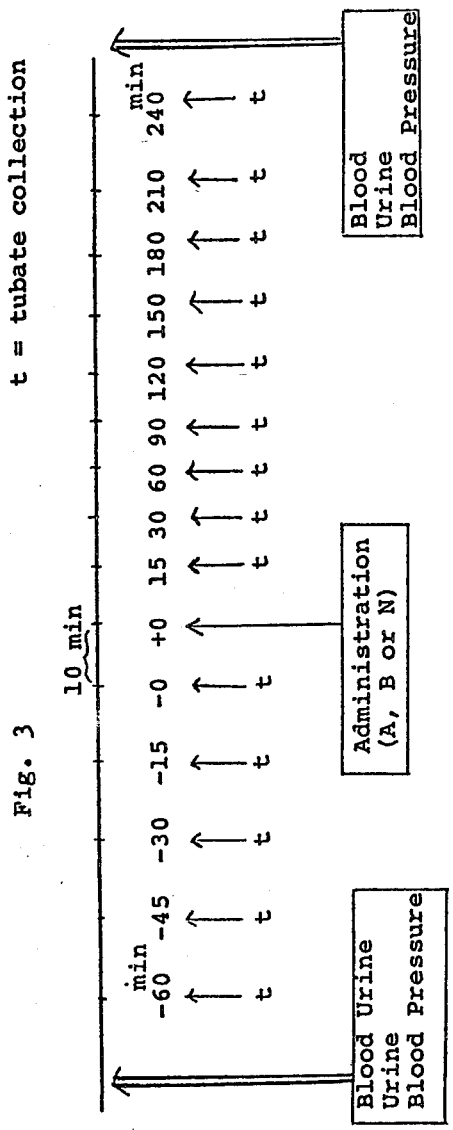

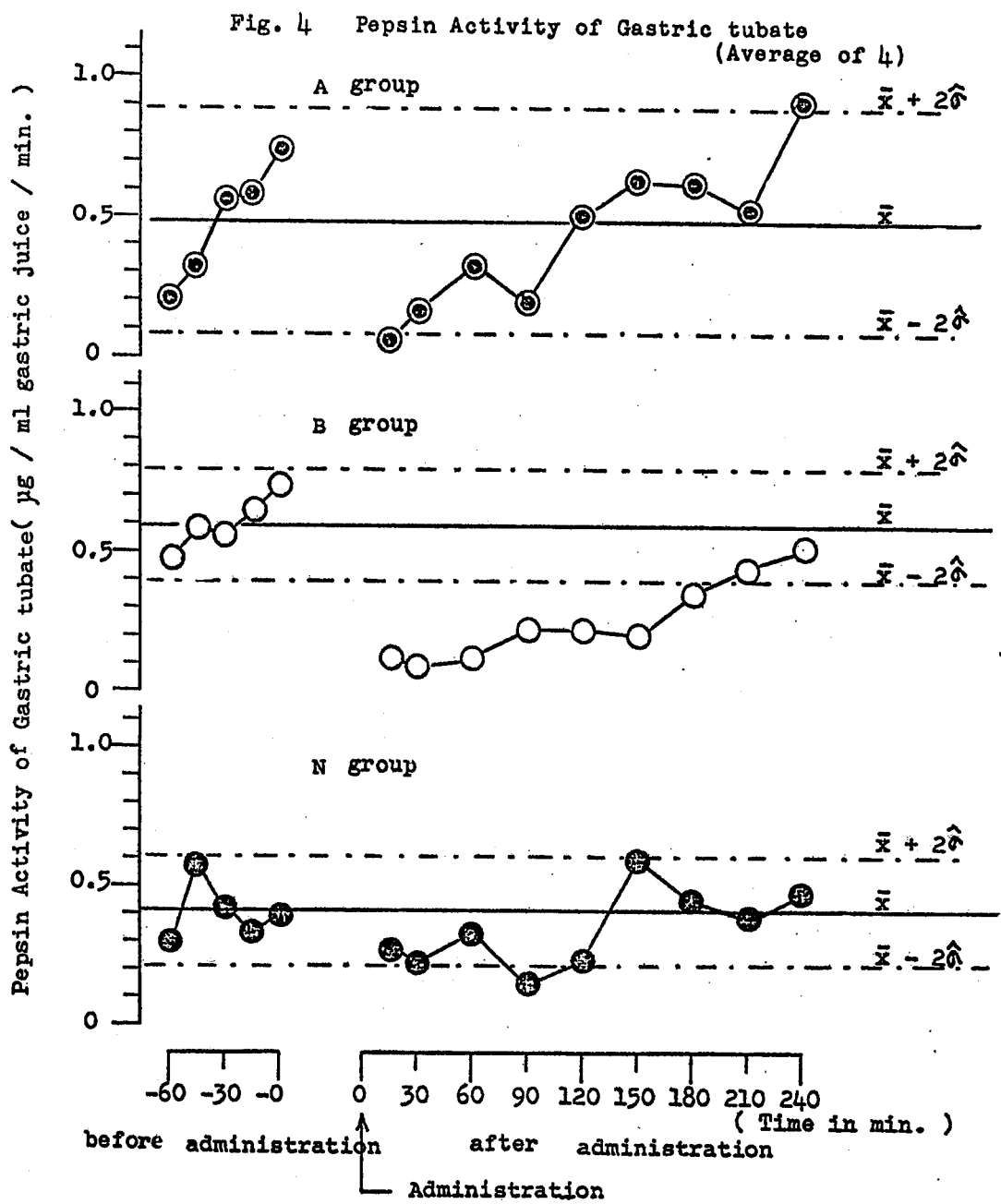

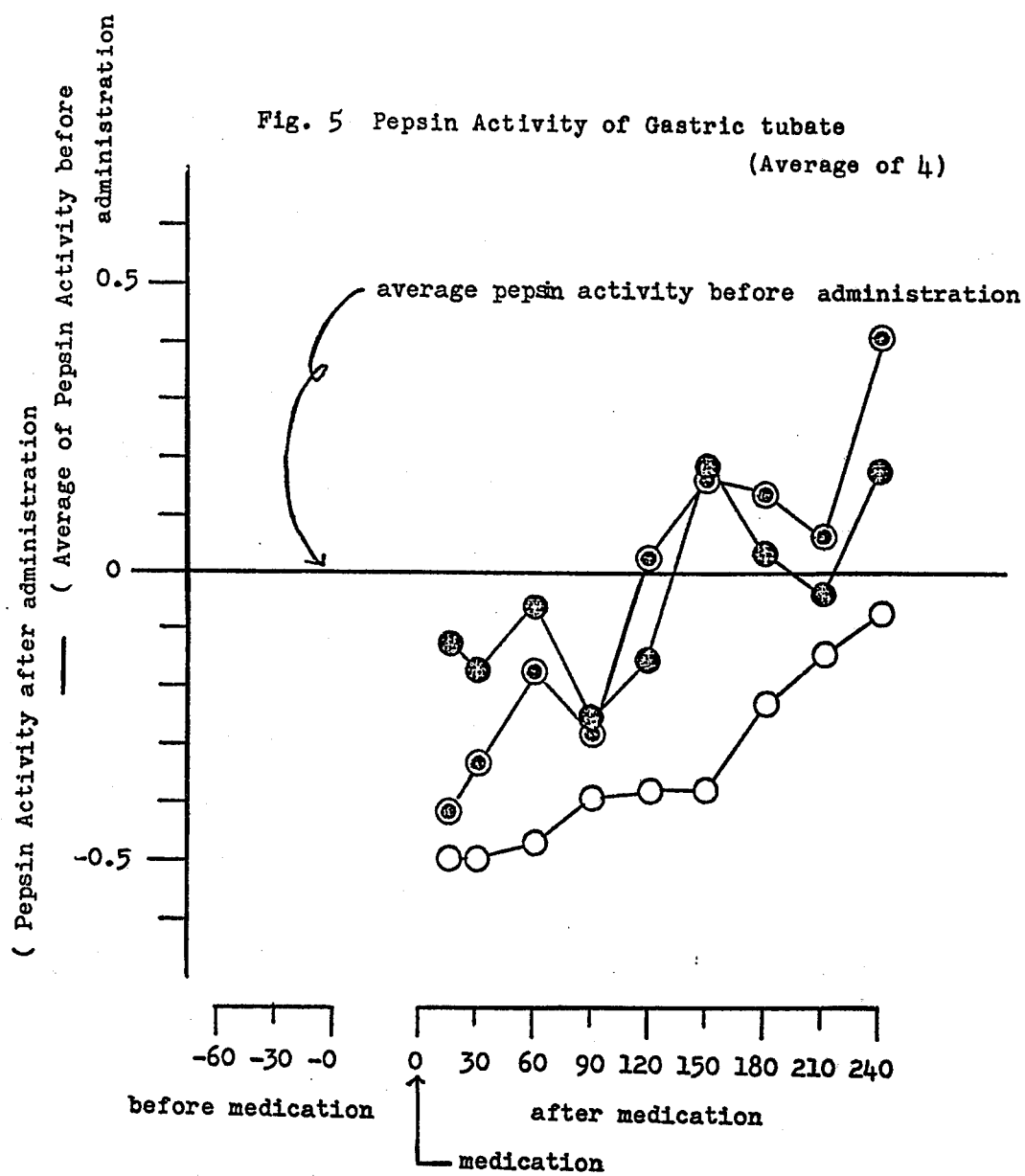

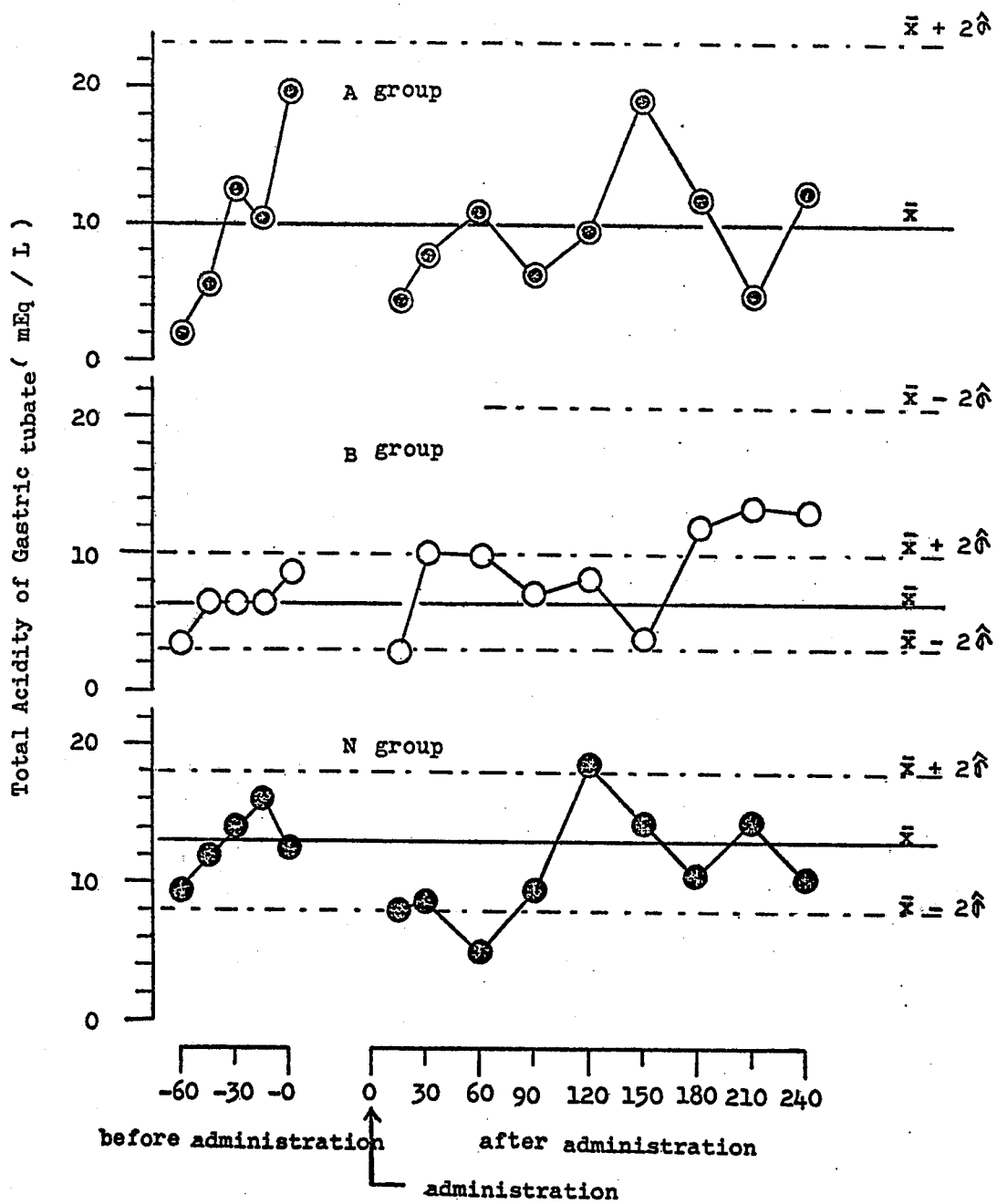
Fig. 6 Total Acidity of Gastric tubate

PROCESS FOR THE PREPARATION OF HOLLOW PARTICULATES

The present invention relates to a process for the preparation of hollow particulates which have hollow spaces therein. More particularly, it relates to a process for the preparation of hollow particulates, comprising spray-drying a system consisting of ethylcellulose and a lower chlorinated hydrocarbon, or spray-drying other systems obtained by further adding a lower chlorofluorinated hydrocarbon and/or water to the former system.

The hollow particulates produced by the present invention may also be prepared by adding other pharmacologically active ingredients to the above systems prior to the spray-drying of the mixture, depending on the intended use.

The hollow particulates produced by the present invention can be applied to many uses, as in the fields of food, agriculture, pharmaceutical industry, and other industries. Above all, the use for medicines is the most important.

For medicines such as, for example, medicines which effect the gastric mucous membrane, medicines which are absorbed by the gastric mucous membrane to exhibit the medical effects, and medicines which effect the gastric juice, it is desirable that the medicines remain in the stomach for a long period of time so that their medical effects may be exhibited over a long period of time. Since there has not yet been discovered a form for medicines suitable for permitting the medicines to remain in the stomach for a long period of time, however, these medicines could not sufficiently exhibit their pharmacological effects.

Accordingly, one of the objects of the present invention is to provide a process for preparing new hollow particulates.

Another object of the present invention is to provide a process for preparing new hollow particulates for gastric medicines and other durable medicines suspendable in the gastric juice and remainable in the stomach for a long period of time, thereby gradually releasing the active ingredient into the gastric juice.

Still a further object of the present invention is to provide a process for the preparation of new hollow particulates, characterized in that ethylcellulose is dissolved in a solvent selected from the group consisting of (A) a lower chlorinated hydrocarbon alone; (B) a mixture of a lower chlorinated hydrocarbon and a lower chlorofluorinated hydrocarbon; (C) a mixture of a lower chlorinated hydrocarbon, a lower chlorofluorinated hydrocarbon and water; and (D) a mixture of a lower chlorinated hydrocarbon and water, so that the concentration of the ethylcellulose is 0.5–4% by weight based on the total weight of the resulting solution, and then spray-drying the solution at an inlet temperature of higher than 50° C.

Other objects and advantages of the present invention will be apparent from the following description.

The hollow particulates produced by the present invention containing pharmacologically active ingredients, are most suitable for gastric medicines such as antacid, anti-pepsin agent, local anesthetic accelerator of gastric motion and the like, since they are floatable and suspendable in the stomach, or they are adsorbed on the wall of the stomach and remain therein for a long period of time, so as to continually release their pharmacologically active ingredient during said period. They are also suitable for durable medicines used in treating all other diseases, since their pharmacologically active ingredients will be gradually released in the organs ranging from the stomach to the intestine.

Lower chlorinated hydrocarbons used in the present invention are in a liquid state at normal temperature and atmospheric pressure, and are exemplified by trichloroethane, methylene chloride, chloroform, carbon tetrachloride, dichloroethane, tetrachloroethane and the like.

Lower chlorofluorinated hydrocarbons used in the present invention are in a liquid or gaseous state at normal temperature. In the latter case, they are used in a liquefied form by applying pressure or by cooling. As the lower chlorofluorinated hydrocarbons, there may be mentioned, for example, trichlorotrifluoroethane, dichlorodifluoromethane, dichlorotetrafluoroethane, trichloromonofluoromethane, dichlorotrifluoroethane, dichlorodifluoroethane, monochlorotrifluoroethane and the like.

The concentration of ethylcellulose in the system is 0.5–4% by weight based on the total weight of the solution. Such concentration is a preferable range for producing suitable hollow particulates.

The concentration of ethylcellulose is calculated by means of the following equation:

$$\text{Concentration of ethylcellulose (\%)} = \frac{\text{weight of ethylcellulose}}{\text{weight of ethylcellulose plus weight of solvent}} \times 100$$

wherein the solvent is a lower chlorinated hydrocarbon or a mixture of a lower chlorinated hydrocarbon, a lower chlorofluorinated hydrocarbon and/or water, that is, (A), (B), (C), or (D) as mentioned above.

If ethylcellulose is used in a concentration of over 4% by weight, thread-like products are formed during spray-drying, and accordingly, it is difficult to form desirable particulates. On the other hand, if ethylcellulose is used in a concentration of below 0.5% by weight, there are formed undesirable particulates having an internal space volume ratio (%) which is too small; such ratio being defined as a ratio of an internally spatial volume of the particulate to the bulk, i.e. the total volume of the particulate.

The spray drying of the solution is carried out at a threshold temperature, that is, an inlet temperature of over 50° C., because the internal space volume ratio (%) of the particulate is too small at a temperature of below 50° C., whereby the desired objects of the invention can not be attained.

According to the present invention, the hollow particulates may also be prepared by adding other materials, for example, pharmacologically active ingredient(s), excipient(s), etc. to the ethylcellulose-containing solution, depending on desired uses. It is however desirable to use said other materials in an amount below 8 times the weight of the ethylcellulose used. When the materials are added in a large amount over 8 times the weight of the ethylcellulose, the internal space volume ratio of the hollow particulates would be reduced, whereby the desired objects of the invention can not be achieved.

According to the process of the present invention, there are prepared spherical hollow particulates having an average diameter of about 10–200μ, an internal space volume ratio more than about 50%, and an apparent density below about 0.7.

FIG. 1 shows a photomicrograph of a cross section of the hollow particulate which was produced according to the process of the present invention. More particularly, the specimen of the particulate for the photomicrograph is prepared by fixing the outside surface of the particulate with paraffin, and then slicing the fixed material. In the Figure, the central circular part shows the internal space of the particulate, and the outer thin layer is the outershell of the particulate.

Figure 2:
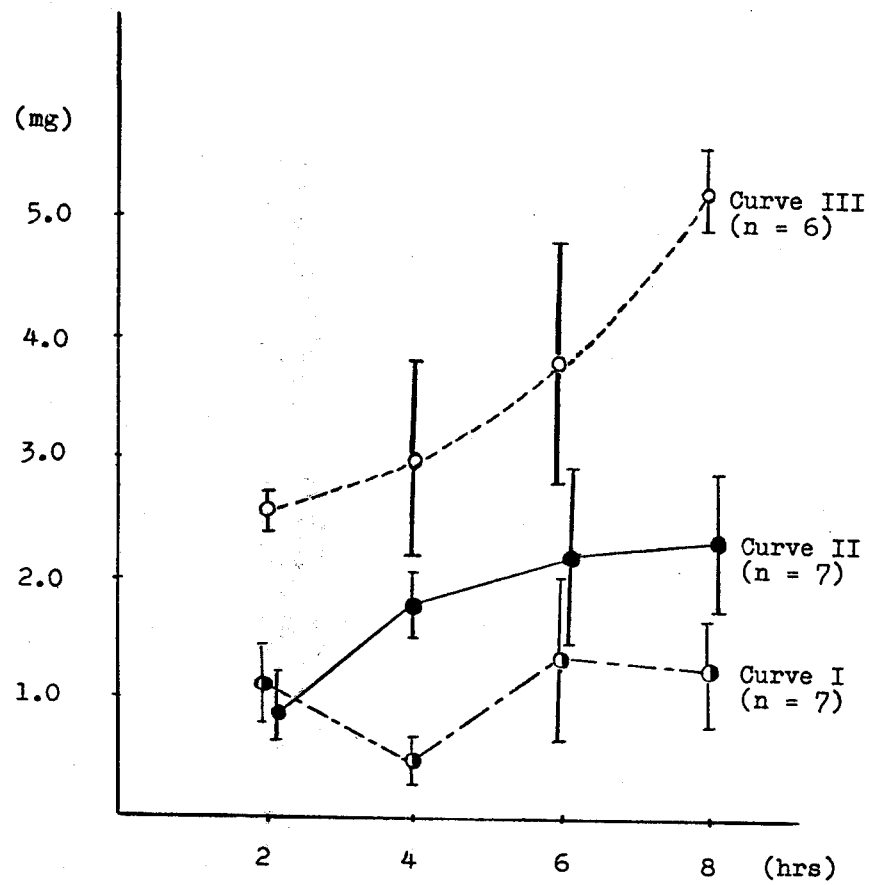

FIG. 2 is a graphical diagram showing a comparison between the particulate produced by the present invention and two controls, with respect to pepsin activity in the gastric juice of rats. In the Figure, Curve I shows the pepsin activity of the particulate containing S-PI powder according to the present invention; Curve II shows that of a control containing S-PI powder and starch; and Curve III shows that of the other control containing starch alone. In the Figure, the longitudinal axis of the coordinates indicates pepsin activity (mg), while the transversal axis indicates time (hour) after administration of the medicines.

FIG. 3 illustrates the schedule wherein blood collection, urine collection and blood pressure measurement were taken before and after the first and the last tubate collections, respectively. In the Figure, "t" means tubate collection.

FIG. 4 demonstrates the figures in the hereinafter-mentioned Table 4 graphically. The range between upper and lower lines show the deviation of pepsin activity before administration (95% reliability). Inhibition of pepsin activity was observed in the B group, but not in the A or the N groups.

FIG. 5 demonstrates the figures calculated by the following formula.

$$\frac{\text{Pepsin activity after administration}}{\text{pepsin activity before administration}} \quad (1)$$

This way the inhibition of pepsin activity in the B group is clearly demonstrated. The A group seems to show inhibition in initial stage.

FIG. 6 shows the total acidity. The total acidity of the B group showed a slight increase in the later stage.

Following Examples will serve to illustrate the invention, but the invention is not restricted by these Examples.

EXAMPLE 1

Hollow particulates were respectively prepared in accordance with the hereinafter mentioned formulations. The process for the preparation of said particulates was carried out by dissolving ethylcellulose in trichloroethane or chloromethane; adding trichlorotrifluoroethane to the resulting solution; and spray-drying the mixture at the inlet temperature of 150° C. For comparison, there were also prepared the formulations for controls wherein the concentrations of ethylcellulose are respectively 14% by weight or above on the basis of the total weight of the respective formulations. These formulations are listed in the following Table 1.

Table 1

| Formulation No. | Ethyl-cellulose (g.) | Trichloro-ethane (g.) | Chloro-methane (g.) | Trichloro-trifluoro-ethane (g.) |
|---|---|---|---|---|
| 1 | 200 | 1,800 | — | — |
| 2 | 200 | 3,800 | — | — |

Table 1-continued

| Formulation No. | Ethyl-cellulose (g.) | Trichloro-ethane (g.) | Chloro-methane (g.) | Trichloro-trifluoro-ethane (g.) |
|---|---|---|---|---|
| 3 | 200 | 4,800 | — | — |
| 4 | 180 | 5,820 | — | — |
| 5 | 200 | 9,800 | — | — |
| 6 | 200 | 19,800 | — | — |
| 7 | 200 | — | 3,800 | — |
| 8 | 200 | — | 4,800 | — |
| 9 | 180 | — | 5,820 | — |
| 10 | 200 | — | 9,800 | — |
| 11 | 200 | 1,800 | — | 2,000 |
| 12 | 200 | 1,800 | — | 3,000 |
| 13 | 280 | 1,620 | — | 4,200 |
| 14 | 200 | 1,800 | — | 8,000 |
| 15 | 200 | — | 1,800 | 2,000 |
| 16 | 200 | — | 1,800 | 3,000 |
| 17 | 180 | — | 1,620 | 4,200 |
| 18 | 200 | — | 1,800 | 8,000 |

The following Table 2 shows forms and internal space volume ratio (%) of the particulates which were prepared in accordance with the above-mentioned respective formulations.

Table 2

| Conc. of ethyl-cellulose in formulation | Ethylcellulose + Trichloroethane | | | Ethylcellulose + Chloromethane | | |
|---|---|---|---|---|---|---|
| | F. No.* | I.S.V.** | Forms | F. No.* | I.S.V.** | Forms |
| 10 | 1 | 65 | thready | — | | |
| 5 | 2 | 67 | " | 7 | 70 | thready |
| 4 | 3 | 64 | " | 8 | 71 | " |
| 3 | 4 | 64 | spherical | 9 | 73 | spherical |
| 2 | 5 | 64 | " | 10 | 80 | " |
| 1 | 6 | 48 | " | | — | |

| Conc. of ethyl-cellulose in formulation | Ethylcellulose + Trichloroethane + Trichlorotrifluoroethane | | | Ethylcellulose + Chloromethane + Trichlorotrifluoroethane | | |
|---|---|---|---|---|---|---|
| | F. No.* | I.S.V.** | Forms | F. No.* | I.S.V.** | Forms |
| 10 | — | | | — | | |
| 5 | 11 | 86 | thready | 15 | 80 | thready |
| 4 | 12 | 85 | " | 16 | 82 | " |
| 3 | 13 | 89 | spherical | 17 | 80 | spherical |
| 2 | 14 | 90 | " | 18 | 81 | " |
| 1 | — | | | — | | |

NOTE:
*F. No.:Formulation No.
**I.S.V.:Internal Space Volume ratio (%)

As shown in the above Table, when the concentration of ethylcellulose in the formulation is more than 4% by weight, thready particulates are prepared, which are not preferable. By comparing the formulations wherein a lower chlorinated hydrocarbon such as trichloroethane or chloromethane is used as a single solvent, with the other formulations wherein a mixture of the lower chlorinated hydrocarbon and a lower chlorofluorinated hydrocarbon such as trichlorotrifluoroethane is used as a mixed solvent, it is observed that particulates having a larger internal space volume ratio can be prepared by using the mixed solvents.

The internal space volume ratio (%) of the particulates is calculated as follows. Apparent density (P) of the particulates is determined by using liquid paraffin as standard substance and a picnometer. The particulate is perfectly ground, and the true density ($P_o$) of constituent material of the particulate is measured with Beckmann-Toshiba Air Comparison Type picnometer, produced and sold by Toshiba Electric Co., Ltd. Japan.

Internal space volume ratio (%) is calculated by means of the following equation:

Internal space volume ratio (%) = $(1 - P/P_o) \times 100$

EXAMPLE 2

In 58.2 Kg of trichloroethane, 1.8 Kg of ethylcellulose were dissolved, and the solution was divided into seven aliquots of the same quantity. Each aliquot was spray-dried at inlet temperature of 50° C., 75° C., 100° C., 125° C., 150° C., 175° C. and 200° C., respectively.

There were thus prepared spherical particulates having diameters of 50–150μ, their internal space volume ratio (%) being as follows:

| Temperature (° C) | Internal space volume ratio (%) |
|---|---|
| 50 | 44 |
| 75 | 52 |
| 100 | 58 |
| 125 | 54 |
| 150 | 63 |
| 175 | 61 |
| 200 | 69 |

EXAMPLE 3

In 58.2 Kg of chloromethane, 1.8 Kg of ethylcellulose were dissolved, and the solution was divided into four aliquots of the same quantity. Each aliquot was spray-dried at inlet temperature of 50° C., 100° C., 150° C. and 200° C., respectively. There are thus prepared spherical particulates having diameters of 50–150μ. Their internal space volume ratios were as follows:

| Temperature (° C) | Internal space volume ratio (%) |
|---|---|
| 50 | 73 |
| 100 | 79 |
| 150 | 73 |
| 200 | 80 |

EXAMPLE 4

In 58.2 Kg of trichloroethane, 1.8 Kg of ethylcellulose were dissolved. The solution was divided to twenty aliquots of the same quantity. Lactose, crystalline cellulose, calcium hydrogenphosphate, or corn starch are added to each aliquot, in amounts of nine times, three times, one time, one third (⅓) and one ninth (1/9), respectively, on the basis of the weight of ethylcellulose. These aliquots are spray-dried at inlet temperature of 150° C. Spherical particulates having diameters of 50–150μ were produced. Their internal space volume ratio (%) were as follows:

| Ratio to ethylcellulose (Times) | Lactose | Crystalline Cellulose | Calcium phosphate dibasic | Corn Starch |
|---|---|---|---|---|
| 9 | 30 | 35 | 63 | 60 |
| 3 | 73 | 63 | 79 | 81 |
| 1 | 39 | 51 | 52 | 50 |
| 1/3 | 51 | 46 | 66 | 82 |
| 1/9 | 51 | 61 | 73 | 84 |

EXAMPLE 5

In 58.2 Kg of trichloroethane, 1.8 Kg of ethylcellulose were dissolved, and the solution was divided into five aliquots of the same quantity. Water is added to each aliquot, in amounts of 0%, 5%, 10%, 20%, and 30%, respectively, by weight, on the basis of the weight of trichloroethane. The resulting aliquots were spray-dried at the inlet temperature of 150° C. Spherical particulates having diameters of 50–150μ were produced. Their space volume ratio (%) were as follows:

| Amount (%) of water added to trichloroethane | Internal space volume ratio (%) of particulate |
|---|---|
| 0 | 64 |
| 5 | 79 |
| 10 | 86 |
| 20 | 87 |
| 30 | 88 |

It is found that the internal space volume ratio is increased in accordance with the weight of water to be added.

EXAMPLE 6

In 5,820 g of trichloroethane, 180 g of ethylcellulose were dissolved, and 600 g of precipitated calcium carbonate were then added to the solution. The mixture was stirred and the resulting homogenized solution was spray-dried at the inlet temperature of 100° C. There are thus prepared spherical particulates having diameters of 50–150μ, their internal space volume ratio being 58%.

EXAMPLE 7

In 3,720 g of trichloroethane, 180 g of ethylcellulose were dissolved. To the solution, 600 g of precipitated calcium carbonate and 2,100 g of trichlorotrifluoroethane was added. The mixture was stirred and the resulting homogenized solution was spray-dried at the inlet temperature of 100° C. Spherical particulates having diameters of 50–150μ were produced. Their internal space volume ratio was 63%.

EXAMPLE 8

In 1,620 g of trichloroethane, 180 g of ethylcellulose were dissolved, and 600 g of precipitated calcium carbonate and 4,200 g of trichlorotrifluoroethane were added to the solution. The mixture was stirred and the resulting homogenized solution was spray-dried at the inlet temperature of 100° C. Spherical particulates having diameters of 50–150μ were produced. Their internal space volume ratio was 66%.

EXAMPLE 9

In 200 ml of water, 10 g of benactyzine hydrochloride were dissolved, and 800 g of 10% ethylcellulose-trichloroethane solution were added to the solution. After mixing, 1,800 g of trichloroethane were added to the mixed solution. The mixture was stirred and the resulting homogenized solution was spray-dried at the inlet temperature of 150° C. Spherical particulates having diameters of 50–150μ were produced. Their internal space volume ratio was 87%.

EXAMPLE 10

In 200 of 3% aqueous sodium carboxymethylcellulose solution, 18 g of benactyzine hydrochloride were dissolved, and then 800 g of 10% ethylcellulose-trichloroethane solution and 1,600 g of trichloroethane were added thereto. The mixture was stirred and the resulting homogenized solution was spray-dried at the inlet temperature of 150° C. Spherical particulates having diameters of 50–150μ were produced. Their internal space volume ratio was 69%.

EXAMPLE 11

In 200 ml of 50% aqueous polyvinylalcohol solution, 30 g of benactyzine hydrochloride were dissolved, and then 800 g of 10% ethylcellulose-trichloroethane solution and 1,800 g of trichloroethane were added thereto. The mixture was stirred and the resulting homogenized solution was spray-dried at the inlet temperature of 150° C. Spherical particulates having diameters of 50–150μ were produced. Their internal space volume ratio of 74%.

EXAMPLE 12

In 200 ml of 12.5% aqueous hydroxypropylcellulose solution, 30 g of benactyzine hydrochloride were dissolved, and then 800 g of 10% ethylcellulose-trichloroethane solution and 1,800 g of trichloroethane were added thereto. The mixture was stirred and the resulting homogenized solution was spray-dried at the inlet temperature of 150° C. Spherical particulates having diameters of 50–150μ were produced. Their internal space volume ratio was 74%.

EXAMPLE 13

In 290 g of water, 10 g of carboxymethylcellulose and 10 g of benactyzine hydrochloride were dissolved, and 800 g of 10% ethylcellulose-trichloroethane solution were added thereto. The mixture was stirred thoroughly. To the solution, there are added 1,800 g of trichloroethane solution having 10 g of Carnauba wax dissolved therein. After the mixture was stirred, the resulting homogenized solution was spray-dried at the inlet temperature of 150° C. Spherical particulates having diameters of 50–150μ were produced. Their internal space volume ratio was 68%.

EXAMPLE 14

In 5,820 g of chloromethane, 180 g of ethylcellulose were dissolved, and 600 g of precipitated calcium carbonate were added thereto. The mixture was stirred and the resulting homogenized solution was spray-dried at the inlet temperature of 100° C. Spherical particulates having diameters of 50–150μ were produced. Their internal space volume ratio was 65%.

EXAMPLE 15

In 5,820 g of chloromethane, 120 g of ethylcellulose and 60 g of hydroxypropylcellulose were dissolved, and 600 g of precipitated calcium carbonate were added thereto. After the mixture was stirred, the resulting homogenized solution was spray-dried at the inlet temperature of 100° C. Spherical particulates having diameters of 50–150μ were produced. Their internal space volume ratio was 66%.

EXAMPLE 16

In 5,820 g of chloromethane, 90 g of ethylcellulose and 90 g of hydroxypropylcellulose were dissolved, and 600 g of precipitated calcium carbonate were added thereto. After the mixture was stirred, the resulting homogenized solution was spray-dried at the inlet temperature of 100° C. There were prepared spherical particulates having diameters of 50–150μ. Their internal space volume ratio was 57%.

EXAMPLE 17

In 300 g of trichloroethane, 10 g of ethylcellulose were dissolved, and 100 g of S-PI (pepsin inhibitor substance; Refer to Agr. Biol. Chem. 35, 8, pp. 1310–1312) were dispersed and suspended in the solution. After 1,000 g of trichlorotrifluoroethane were added to the suspension and mixed therein, the mixed solution was spray-dried at the inlet temperature of 110° C. There were prepared spherical particulates having diameters of 50–150μ, apparent density of about 0.45 and internal space volume ratio of 70%.

S-PI elution tests of these particulates were carried out by using artificial gastric juice (Refer to Japanese Pharmacopoeia, the 8th edition, Part 1, pp. 844). The procedure comprises the following steps: permitting 1 l of artificial gastric juice to stand in a 1 l beaker at the temperature of 37° C.; stirring it under the condition of 120 r.p.m. with a screw consisting of four vanes, each of which has a diameter of 5.5 cm and height of 1 cm; adding the particulates obtained by the afore-mentioned process to the artificial gastric juice; sampling the resulting solution at the predetermined time to measure an amount of S-PI eluted; and calculating elution ratio from the total amount of S-PI in the particulates. Elution ratio in the following examples are calculated according to this procedure.

| Elution time (minute) | 5 | 10 | 15 | 30 | 60 | 120 | 180 |
|---|---|---|---|---|---|---|---|
| Elution ratio (%) | 29 | 40 | 60 | 68 | 79 | 85 | 90 |

EXAMPLE 18

In 112.5 g of trichloroethane, 12.5 g of ethylcellulose were dissolved, and 375 g of 10% hydroxypropylcellulosechloromethane solution were added thereto and mixed therein. To the mixture, there are added 50 g of S-PI (refer to Example 17), 600 g of trichloroethane, 1 g of fine powder of silicic anhydride and 1,200 g of trichlorotrifluoroethane. The mixture was stirred and the resulting homogenized suspension was spray-dried at the inlet temperature of 100° C. There were prepared spherical particulates having diameters of 50–150μ and internal space volume ratio of 68%.

Elution test of S-PI from the particulates was similarly carried out as mentioned in Example 17. The results are shown in the following table.

| Elution time (minute) | 5 | 10 | 20 | 40 | 80 | 160 |
|---|---|---|---|---|---|---|
| Elution ratio (%) | 27 | 73 | 87 | 90 | 96 | 100 |

EXAMPLE 19

In 4,500 g of trichloroethane, 500 g of ethylcellulose were dissolved, and 500 g of fine barium sulfate powder were dispersed and suspended therein. To the suspension, there were added 5,000 g of trichlorotrifluoroethane, and after mixing, the resulting homogenized solution was spray-dried at the inlet temperature of 150° C. There were thus prepared spherical particulates having diameters of 50–150μ, internal space volume ratio of 93%, and apparent density of 0.19.

EXAMPLE 20

In 450 g of trichloroethane, 50 g of ethylcellulose were dissolved. To the solution, there were added 50 g of S-PI powder (refer to Example 17), 125 mg of silicic anhydride, and 1,200 g of trichloroethane. After mixing, the resulting homogenized solution was spray-dried at the inlet temperature of 150° C. There were prepared spherical particulates having apparent density of 0.700, internal space volume ratio of 46%, and diameters of 50–150μ. Elution ratio of S-PI from the particulates was 66% in 60 minutes.

EXAMPLE 21

In 45 g of trichloroethane, 50 g of ethylcellulose were dissolved. To the solution, there were added 50 g of S-PI powder (refer to Example 17), 125 mg of silicic anhydride, 160 g of water, and 1,200 g of trichloroethane. After mixing, the homogenized solution was spray-dried at the inlet temperature of 150° C. There were prepared spherical particulates having apparent density of 0.355, internal space volume ratio of 73%, and diameters of 50–150μ. Elution ratio of S-PI from the particulates was 54% in 60 minutes.

EXAMPLE 22

In 450 g of trichloroethane, 50 g of ethylcellulose were dissolved. To the solution, there were added 50 g of S-PI powder (refer to Example 17), 125 mg of silicic anhydride, 165 g of 3% aqueous tartaric acid solution, and 1,200 g of trichloroethane. After mixing, the homogenized solution was spray-dried at the inlet temperature of 150° C. There were prepared spherical particulates having apparent density of 0.207, internal space volume ratio of 84%, and diameters of 50–150μ. Elution ratio from these particulates was 44% in 60 minutes.

EXAMPLE 23

In 450 g of trichloroethane, 50 g of ethylcellulose were dissolved. To the solution, there were added 50 g of S-PI powder (refer to Example 17), 125 mg of silicic anhydride, and 1,200 g of trichlorotrifluoroethane. After mixing, the homogenized solution was spray-dried at the inlet temperature of 150° C. There were prepared spherical particulates having apparent density of 0.145, internal space volume ratio of 89%, and diameters of 50–150μ. Elution ratio of S-PI from the particulates was 46% in 60 minutes.

EXAMPLE 24

In 450 g of trichloroethane, 50 g of ethylcellulose were dissolved. To the solution, there were added 50 g of S-PI powder (refer to Example 17), 125 mg of silicic anhydride, 160 g of water and 1,200 g of trichlorotrifluoroethane. After mixing, the homogenized solution was spray-dried at the inlet temperature of 150° C. There were thus prepared spherical particulates having present density of 0.164, internal space volume ratio of 87%, and diameters of 50–150μ. Elution ratio of S-PI from the particulates was 52% in 60 minutes.

EXAMPLE 25

In 450 g of trichloroethane, 50 g of ethylcellulose were dissolved. To the solution, there were added 50 g of S-PI powder (refer to Example 17), 125 mg of silicic anhydride, 165 g of 3% aqueous tartaric acid solution and 1,200 g of trichlorotrifluoroethane. After mixing, the homogenized solution was spray-dried at the inlet temperature of 150° C. There were prepared spherical particulates having apparent density of 0.174, internal space volume ratio of 87%, and diameters of 50–150μ. Elution ratio of S-PI from the particulates was 45% in 60 minutes.

EXAMPLE 26

According to the hereinafter mentioned formulations and processes, there were prepared spherical hollow particulates having diameters of 50–150μ. Elution ratio of S-PI from these particulates were determined.

The preparations of the particulates were carried out by dissolving ethylcellulose in trichloroethane, adding S-PI powder (refer to Example 17), trichlorotrifluoroethane and silicic anhydride thereto, mixing, and spray-drying the homogenized mixture at the inlet temperature of 150° C.

| | FORMULATION | | | |
|---|---|---|---|---|
| Formulation No. | 1 (90%S-PI) | 2 (75%S-PI) | 3 (50%S-PI) | 4 (25%S-PI) |
| Ethylcellulose | 10g | 25g | 50g | 25g |
| S-PI | 90g | 75g | 50g | 75g |
| Trichloroethane | 90g | 225g | 450g | 675g |
| Trichlorotrifluoroethane | 1,900g | 2,000g | 1,600g | 1,500g |
| Silicic anhydride | — | — | 1g | 1g |

| Elution ratio (numerical values are %) | | | | |
|---|---|---|---|---|
| (Time of elution (minute) | Sample Formulation No. | | | |
| | 1 | 2 | 3 | 4 |
| 30 | 67 | 54 | 45 | 30 |
| 60 | 79 | 65 | 67 | 42 |
| 120 | 85 | 72 | 89 | 54 |
| 180 | 86 | 75 | 96 | 65 |

EXAMPLE 27

In 565 g of trichloroethane, 62.5 g of ethylcellulose were dissolved. To the solution, there were added 25 g of oxethazaine (N, N-bis[N-methyl-N-phenyl-tert-butylacetamido]-β-hydroxyethylamine), 12.5 g of silicic anhydride, and 1,400 g of trichlorotrifluoroethane. After mixing, the homogenized solution was spray-dried at the inlet temperature of 75° C. There are prepared spherical particulates having apparent density of 0.250, internal space volume ratio of 78%, and diameters of 50–150μ.

EXAMPLE 28

In 900 g of trichloroethane, 100 g of ethylcellulose were dissolved. To the solution, there are added 100 g of basic aluminum magnesium carbonate, 1 g of silicic anhydride, and 5,000 g of trichlorotrifluoroethane. After mixing, the homogenized solution was spray-dried at the entrance temperature of 100° C. There are prepared spherical particulates having apparent density of 0.357, internal space volume ratio 84% and diameters of 50–150μ.

The hollow particulates prepared according to the process of the invention were administered per os to man and rats, and their residence in the stomach and inhibitory effects for pepsin are observed, which are illustrated in the following experiment.

EXPERIMENT 1

Residence in the stomach of man

The particulates containing 50% barium sulfate, prepared in the aforementioned Example 19, (diameter of 50–150μ, internal space volume ratio of 93%, and apparent density of 0.19) were administrated per os to six men. After administration, X-ray photographs were taken with the lapse of time, in order to trace the movement of the particulates. Residence time in the stomach is defined by the period of the time ranging from the time when the particulates are administered, to the time when the particulates were no longer visible in the stomach. For the control, there were simultaneously administered flat tablets which are soluble in the intestine and have a diameter of about 8 mm. Results are shown in the following table.

Table 3

| Sex distinction | Age | Posture | Administration | Symptoms | Residence time in the stomach (minute) | |
|---|---|---|---|---|---|---|
| | | | | | Particulate of this invention | Tablet of barium sulfate |
| Female | 72 | Supine | After meal | Chronic gastritis | 150 | 60 |
| Male | 76 | Free | Empty stomach | Gastric ulcer | more than 240 | 60 |
| Male | 59 | Free | Empty stomach | Gastric ulcer | 60 | 30 |
| Male | 46 | Free | Empty stomach | Gastric ulcer | 120 | 20 |
| Female | 54 | Free | After meal | Chronic gastritis | more than 240 | 180 |
| Female | 51 | Free | After meal | Chronic gastritis | more than 240 | 120 |

As shown in the above Table 3, the particulates of the present invention have much longer residence time in the stomach as compared with residence time of the tablets of barium sulfate, although there are individual differences.

Experiment 2

Inhibitory Effect for Pepsin in Rats

The particulates (diameter of 50–150μ, internal space volume ratio of 70%, and apparent density of about 0.45) containing S-PI (refer to Example 17) prepared in Example 23 were administered per os in the amount of 100 mg/Kg to male rat of the Wistar strain weighing 200–300 g which was fasted 20 hours. Samples of the gastric juice were taken by Test meal method with the lapse of time, and pepsin activity was determined by the method similar to Bonfils method. Pepsin activity is expressed as the amount (mg) of free tyrosine, and its numerical value is shown by figures of average value ± standard error.

For the control, there were selected starch alone, and a mixture of starch and S-PI powder (the contents of S-PI are same as the particulates containing S-PI mentioned above).

Results are shown in FIG. 2, wherein the longitudinal axis of the coordinate indicates the pepsin activity (mg), and the transversal axis of the coordinate indicates the period of the time (hour) after administration, and n is the number of rats used.

As obvious from FIG. 2, pepsin inhibitory effect of the hollow particulates containing S-PI of the present invention is not only superior to that of the particulates containing starch alone, but also that of the particulates containing a mixture of starch and S-PI powder.

The following clinical data shown inhibitory effects for pepsin, when the hollow particulates prepared according to the process of the invention were administered per os to man.

CLINICAL DATA

I. Preface

The effect of S-PI and hollow particulates containing S-PI of this invention (obtained by Example 23) on antipeptic activity, total acidity and PH were studied in 6 healthy male volunteers and was compared to that of a placebo. Also studied at the same time are the general factors (haematochemistry, urinalysis, blood pressure and subjective symptoms) routinely measured in clinical pharmacological trials.

II. Methods:

Selection of Volunteer

Six healthy male volunteers ranging in age from 28 to 42 and body weight from 58 kg to 72 kg.

Preparations and composition

Preparation A, B and N, which were identical in appearance were coded. Their compositions were as follows:

| Composition | Preparation | | |
|---|---|---|---|
| | A | B | N |
| S-PI | 25.0 mg | — | — |
| Hollow particulate containing S-PI (obtained by Example 23) | — | 50.0 mg | — |
| Potato Starch | 472.5 mg | 447.5 mg | 497.5 mg |
| Colloidal Silica | 2.5 mg | 2.5 mg | 2.5 mg |
| Total: | 500.0 mg | 500.0 mg | 500.0 mg |

Randomizing

With a 2 week interval, two tests were made in which each volunteer was designed to receive differently-coded preparations with physicians and volunteers kept blind as concerns the ingredients. Opening the code after the experiment revealed the following:

| Volunteer No. | (Initial of Name, Age, Weight) | 1st test | 2nd test |
|---|---|---|---|
| No. 1 | (S.W. 31, 75 kg) | A | B |
| 2 | (Y.A. 27, 60 kg) | A | N |
| 3 | (T.K. 42, 60 kg) | B | N |
| 4 | (K.O. 37, 59 kg) | B | A |
| 5 | (M.I. 28, 63 kg) | N | B |
| 6 | (K.K. 35, 58 kg) | N | A |

Items

Items measured in this study were as follows:
a) Gastric tubates:
   Antipeptic activity   Modified Anson's method
   Total acidity   Modified Topfer - Michaelis method
   PH   PH meter (TOA HM-5B)
b) General factors:
   i) Haematochemistry
      GOT, GPT, AL-P, BUN, Billirubin, RBC, WBC, Hb, Ht, MCV, MCH and MCC -continued

| Volunteer No. | (Initial of Name, Age, Weight) | 1st test | 2nd test |
|---|---|---|---|
| | ii) Urinalysis Protein and Sugar iii) Blood pressure iv) Subjective Symptoms | | |

Procedure

Volunteers were fasted at least 12 hrs before administration. Water intake was allowed. Gastric tubates were collected in a volume of 2-3 ml 14 times altogether; five times before administration with 15 minute intervals and 9 times after administration (15, 30, 60, 90, 120, 150, 180, 210 and 240 minutes). Administration of each preparation was made 10 minutes after the last tubate collection before administration. FIG. 3 illustrates the schedule wherein blood collection, urine collection, and blood pressure measurement were taken before and after the first and the last tubate collections, respectively.

Each subject recorded subjective symptons, if any, on a record sheet twice before administration at a 1 hr interval, 3 times after administration at 2 hr intervals, and 24 hrs after administration.

All through the experiments, volunteers stayed in a sitting position and avoided excessive movements.

Dosing 500 g of preparation A, B or N was administered with 100 cc of water directly into the stomach through tubing.

III. Results:
 (a) Gastric tubates
 See Table 4.

PA and TA means pepsin activity and total acidity respectively.

PA ... ug/ml gastric juice/min
TA ... mEg/L

FIG. 4 demonstrates the figures in Table 4 graphically. The range between upper and lower lines show the deviation of pepsin activity before administration (95% reliability). Inhibition of pepsin activity was observed in the B group, but not in the A or the N groups.

FIG. 5 demonstrates the figures calculated by the following formula $$\frac{\text{Pepsin activity after administration}}{\text{pepsin activity before administration}} \quad (1)$$

This way the inhibition of pepsin activity in the B group is clearly demonostrated. The A group seems to show inhibition in the initial stage.

FIG. 6 shows the total acidity. The total acidity of the B group showed slight increase in the later stage.

(b) General factors:
(i) Haematochemistry
All parameters were within normal range. see Table 5.
(ii) Urinalysis
All parameters were within normal range. See Table 6.
(iii) Blood pressure
Blood pressure remained within normal range. See Table 7.
(iv) Subjective symptoms
No abnormal findings in the record sheet such as abdominal discomfort, gastric pain, headache, vertigo, ear ringing, limb numbness, perspiration, skin rash, sense of fever, or dry mouth were observed.
No complaints of other symptoms.

Table 4

| Test Group | Test No. | Volunteer's Number | Items | before administration (min.) | | | | |
|---|---|---|---|---|---|---|---|---|
| | | | | −60 | −45 | −30 | −15 | −0 |
| A | 1 | 1 | PA | 149 | 501 | 465 | 229 | 626 |
| | | | PH | 6.5 | 2.7 | 2.5 | 5.9 | 2.3 |
| | | | TA | — | 9.4 | 10.9 | — | 9.8 |
| | 1 | 2 | PA | 14 | 7 | 25 | 4 | 0 |
| | | | PH | 8.0 | 8.0 | 8.3 | 8.4 | 7.5 |
| | | | TA | — | — | — | — | — |
| | 2 | 4 | PA | 61 | 108 | 744 | 884 | 864 |
| | | | PH | 7.2 | 7.0 | 2.7 | 2.2 | 1.7 |
| | | | TA | — | — | 11.2 | 11.4 | 23.2 |
| | 2 | 6 | PA | 631 | 655 | 972 | 1153 | 1422 |
| | | | PH | 3.9 | 2.4 | 2.7 | 1.4 | 1.4 |
| | | | TA | 7.2 | 12.2 | 28.6 | 29.8 | 44.8 |
| B | 1 | 3 | PA | 17 | 14 | 0 | 7 | 0 |
| | | | PH | 7.5 | 8.5 | 8.5 | 8.5 | 8.1 |
| | | | TA | — | — | — | — | — |
| | 1 | 4 | PA | 169 | 517 | 379 | 463 | 728 |
| | | | PH | 7.0 | 3.4 | 4.8 | 6.0 | 4.9 |
| | | | TA | — | 11.4 | 3.6 | — | 4.6 |
| | 2 | 1 | PA | 259 | 767 | 820 | 780 | 784 |
| | | | PH | 3.6 | 2.4 | 2.0 | 1.8 | 1.7 |
| | | | TA | 6.8 | 6.2 | 10.4 | 12.4 | 17.6 |
| | 2 | 5 | PA | 1395 | 1018 | 928 | 1284 | 1396 |
| | | | PH | 3.1 | 2.6 | 2.5 | 2.4 | 2.7 |
| | | | TA | 8.0 | 8.2 | 12.0 | 13.8 | 11.6 |
| N | 1 | 5 | PA | 460 | 1424 | 1330 | 1062 | 1114 |
| | | | PH | 3.7 | 1.9 | 1.8 | 1.7 | 2.0 |
| | | | TA | 9.8 | 22.2 | 34.2 | 43.8 | 23.6 |
| | 1 | 6 | PA | 136 | 14 | 59 | 101 | 223 |
| | | | PH | 1.5 | 1.3 | 1.3 | 1.3 | 1.5 |
| | | | TA | 24.6 | 24.8 | 23.0 | 22.0 | 27.2 |
| | 2 | 3 | PA | 19 | 38 | 26 | 26 | 38 |
| | | | PH | 7.8 | 6.8 | 6.6 | 7.5 | 7.7 |
| | | | TA | — | — | — | — | — |
| | 2 | 2 | PA | 576 | 737 | 262 | 192 | 208 |
| | | | PH | 5.5 | 6.3 | 6.2 | 7.1 | 6.5 |
| | | | TA | 4.4 | 0.4 | — | — | — |

| Test Group | Test No. | Volunteer's Number | Items | after administration (min.) | | | | | | | |
|---|---|---|---|---|---|---|---|---|---|---|---|
| | | | | 15 | 30 | 60 | 90 | 120 | 150 | 180 | 210 | 240 |

Table 4-continued

| | | | | | | | | | | | | |
|---|---|---|---|---|---|---|---|---|---|---|---|---|
| | 1 | 1 | PA | 39 | 15 | 114 | 18 | 412 | 286 | 368 | 691 | 977 |
| | | | PH | 2.3 | 1.9 | 1.8 | 1.6 | 2.3 | 1.8 | 2.0 | 2.0 | 1.9 |
| | | | TA | 6.2 | 14.6 | 18.0 | 24.8 | 8.8 | 17.6 | 11.4 | 15.4 | 16.6 |
| A | 1 | 2 | PA | 14 | 4 | 7 | 0 | 69 | 86 | 82 | 517 | 479 |
| | | | PH | 7.3 | 7.1 | 7.5 | 7.5 | 7.3 | 8.1 | 8.2 | 7.6 | 7.7 |
| | | | TA | — | — | — | — | — | — | — | — | — |
| | 2 | 4 | PA | 100 | 362 | 884 | 679 | 904 | 1153 | 904 | 767 | 1266 |
| | | | PH | 2.0 | 1.6 | 1.7 | — | 1.9 | 1.9 | 2.3 | 3.8 | 2.2 |
| | | | TA | 6.0 | 10.2 | 16.4 | — | 14.4 | 18.6 | 14.8 | 3.6 | 13.2 |
| | 2 | 6 | PA | 120 | 201 | 201 | 81 | 622 | 1048 | 1109 | 173 | 948 |
| | | | PH | 1.9 | 1.7 | 1.7 | 6.5 | 1.8 | 1.4 | 1.4 | 6.2 | 1.7 |
| | | | TA | 5.8 | 4.8 | 9.6 | — | 14.6 | 39.2 | 19.4 | — | 18.6 |
| | 1 | 3 | PA | 0 | 0 | 0 | 55 | 0 | 0 | 0 | 0 | 17 |
| | | | PH | 7.7 | 7.7 | 7.5 | 6.4 | 7.8 | 8.3 | 7.9 | 7.8 | 7.8 |
| | | | TA | 4.8 | — | — | 1.6 | — | — | — | — | — |
| B | 1 | 4 | PA | — | 111 | 317 | 214 | 200 | 483 | 558 | 517 | 355 |
| | | | PH | — | 2.5 | 2.1 | 3.2 | 5.8 | 6.3 | 3.9 | 2.8 | 5.8 |
| | | | TA | — | 8.8 | 15.0 | 6.2 | — | 0.6 | 6.4 | 16.8 | — |
| | 2 | 1 | PA | 97 | 97 | 0 | 76 | 25 | 79 | 68 | 21 | 572 |
| | | | PH | 1.9 | 1.7 | 1.5 | 1.6 | 1.5 | 1.5 | 1.5 | 1.6 | 1.7 |
| | | | TA | 4.2 | 14.8 | 14.6 | 4.6 | 15.0 | 16.0 | 23.6 | 19.2 | 25.0 |
| | 2 | 5 | PA | 208 | 165 | 187 | 460 | 625 | 270 | 787 | 1259 | 1129 |
| | | | PH | 2.2 | 2.0 | 2.1 | 1.8 | 2.3 | 5.7 | 3.1 | 2.0 | 1.8 |
| | | | TA | 3.8 | 16.6 | 10.8 | 17.2 | 18.0 | 0.2 | 14.8 | 19.8 | 28.8 |
| | 1 | 5 | PA | 749 | 637 | 853 | 341 | 755 | 1149 | 940 | 1041 | 1260 |
| | | | PH | 2.0 | 2.0 | 2.0 | 6.5 | 4.1 | 1.9 | 2.0 | 1.7 | 2.3 |
| | | | TA | 14.2 | 15.4 | 16.0 | 3.2 | 6.4 | 21.0 | 21.0 | 32.4 | 16.6 |
| | 1 | 6 | PA | 142 | 191 | 289 | 70 | 49 | 55 | 564 | 188 | 240 |
| N | | | PH | 1.6 | 1.5 | — | 1.2 | 1.1 | 1.1 | 1.4 | 1.3 | 1.4 |
| | | | TA | 19.4 | 19.2 | — | 35.6 | 66.4 | 36.4 | 22.0 | 26.8 | 25.4 |
| | 2 | 3 | PA | 7 | 19 | 38 | 0 | 0 | 0 | 31 | 19 | 92 |
| | | | PH | 6.9 | 6.7 | 6.2 | 6.4 | 6.1 | 7.5 | 6.3 | 7.5 | 7.1 |
| | | | TA | — | — | 4.4 | — | 1.8 | — | — | — | — |
| | 2 | 2 | PA | 215 | 38 | 115 | 192 | 172 | 1194 | 268 | 211 | 768 |
| | | | PH | 6.3 | 6.9 | 6.5 | 6.2 | 7.3 | 6.3 | 7.0 | 7.3 | 6.3 |
| | | | TA | — | — | — | — | — | 1.0 | — | — | — |

Table 5

| | | GOT | | GPT | | ALP | | Billi rubin | | BUN | | RBC | |
|---|---|---|---|---|---|---|---|---|---|---|---|---|---|
| Case No. | | Before | After | Before | After | Before | After | Before | After | Before | After | Before | After |
| 1 | 1st | 22.5 | 26.5 | 20 | 18 | 8.6 | 8.5 | 0.74 | 0.72 | 14.7 | 15.2 | 391 | 415 |
| | 2nd | 18.0 | 18.0 | 18.5 | 16.0 | 9.9 | 9.1 | 0.76 | 0.79 | 13.8 | 15.1 | 484 | 450 |
| 2 | 1st | 42.5 | 40 | 42 | 40 | 11.8 | 11.5 | 1.85 | 2.32 | 16.2 | 15.4 | 412 | 460 |
| | 2nd | 33.5 | 28.0 | 33 | 13.5 | 11.9 | 12.1 | 2.02 | 2.77 | 16.1 | 16.5 | 450 | 485 |
| 3 | 1st | 23 | 24 | 17 | 19 | 9.0 | 8.0 | 0.53 | 0.84 | 12.8 | 12.0 | 446 | 400 |
| | 2nd | 21.0 | 17.0 | 17.0 | 14.0 | 9.9 | 9.7 | 0.79 | 1.04 | 13.2 | 14.4 | 250 | 443 |
| 4 | 1st | 60 | 52 | 69 | 72 | 10.9 | 9.8 | 1.25 | 1.76 | 16.4 | 16.3 | 629 | 648 |
| | 2nd | 44 | 30 | 40 | 27 | 8.4 | 7.7 | 0.88 | 1.02 | 18.8 | 17.9 | 584 | 647 |
| 5 | 1st | 22.5 | 16.5 | 22 | 17 | 5.8 | 5.4 | 2.40 | 2.22 | 8.6 | 10.9 | 483 | 467 |
| | 2nd | 19.0 | 14.5 | 18.5 | 16.0 | 7.7 | 7.7 | 2.95 | 3.19 | 11.8 | 16.8 | 500 | 424 |
| 6 | 1st | 38 | 37 | 28 | 29 | 8.4 | 8.6 | 1.05 | 1.10 | 11.9 | 12.1 | 383 | 375 |
| | 2nd | 38 | 35 | 25 | 20 | 7.1 | 7.7 | 0.80 | 0.85 | 12.8 | 13.4 | 390 | 529 |

| | | WBC | | Hb | | Ht | | MCV | | MCH | | MCC | |
|---|---|---|---|---|---|---|---|---|---|---|---|---|---|
| Case No. | | Before | After | Before | After | Before | After | Before | After | Before | After | Before | After |
| 1 | 1st | 5200 | 5900 | 14.7 | 14.4 | 45.5 | 45 | 116.0 | 108.4 | 37.5 | 34.7 | 32.3 | 32.1 |
| | 2nd | 1050 | 800 | 11.2 | 12.6 | — | — | — | — | 23.2 | 28 | — | — |
| 2 | 1st | 2200 | 3800 | 14.2 | 15.0 | 42 | 43.5 | 102.0 | 94.6 | 34.5 | 32.6 | 33.8 | 34.5 |
| | 2nd | 1400 | 2000 | 11.8 | 14.8 | — | — | — | — | 26.3 | 30.5 | — | — |
| 3 | 1st | 3800 | 5400 | 13.3 | 10.2 | 40 | 36 | 89.6 | 90.0 | 29.8 | 25.5 | 36.3 | 28.3 |
| | 2nd | 900 | 1200 | 11.9 | 14.1 | — | — | — | — | 47.5 | 31.8 | — | — |
| 4 | 1st | 3300 | 3300 | 20.4 | 20.1 | 65 | 63 | 103.5 | 97.4 | 32.5 | 31.0 | 31.4 | 32.0 |
| | 2nd | 4800 | 5200 | 18.2 | 19.2 | 57 | 62.5 | 97.4 | 95.1 | 31.3 | 29.7 | 31.9 | 30.7 |
| 5 | 1st | 4700 | 4600 | 15.7 | 12.9 | 50 | 41 | 103.5 | 87.8 | 34.6 | 27.6 | 33.5 | 31.5 |
| | 2nd | 1100 | 1300 | 20.7 | 15.6 | — | — | — | — | 41.3 | 36.8 | — | — |
| 6 | 1st | 3200 | 3400 | 11.0 | 10.5 | 33 | 35 | 86.2 | 93.2 | 28.8 | 28.0 | 33.4 | 30.0 |
| | 2nd | 3200 | 4800 | 12.2 | 15.1 | 38.5 | 49 | 98.9 | 93 | 31.3 | 28.7 | 31.7 | 30.8 |

Table 6

| b) ii) Urinalysis | | Protein | | Sugar | |
|---|---|---|---|---|---|
| Case No. | | Before | After | Before | After |
| No. 1 | 1st | — | — | — | — |
| | 2nd | — | — | — | — |
| No. 2 | 1st | — | — | — | — |
| | 2nd | — | — | — | — |
| No. 3 | 1st | — | — | — | — |
| | 2nd | — | — | — | — |
| No. 4 | 1st | — | — | — | — |
| | 2nd | — | — | — | — |
| No. 5 | 1st | — | — | — | — |
| | 2nd | + | — | — | — |
| No. 6 | 1st | — | — | — | — |
| | 2nd | — | — | — | — |

Table 7

| b) iii) Blood pressure | | | |
|---|---|---|---|
| Case No. | | Before | After |
| No. 1 | 1st | 114/86 | 108/74 |
| | 2nd | 98/70 | 108/80 |
| No. 2 | 1st | 110/84 | 100/82 |
| | 2nd | 110/70 | 126/92 |
| No. 3 | 1st | 96/60 | 92/60 |
| | 2nd | 106/52 | 108/86 |
| No. 4 | 1st | 160/112 | 156/114 |
| | 2nd | 152/110 | 150/111 |
| No. 5 | 1st | 112/72 | 112/66 |
| | 2nd | 124/68 | 114/68 |
| No. 6 | 1st | 132/86 | 122/78 |
| | 2nd | 120/80 | 121/79 |

From the foregoing clinical data, it may be understood that the hollow particulates according to the present invention are the most suitable for the medical form containing S-PI.

What is claimed is:

1. A process for preparing spherical, hollow particulates, which comprises dissolving ethylcellulose in a solvent selected from the group consisting of a lower chlorinated hydrocarbon, a mixture of a lower chlorinated hydrocarbon and a lower chlorofluorinated hydrocarbon, a mixture of a lower chlorinated hydrocarbon, a lower chlorofluorinated hydrocarbon and water, and a mixture of a lower chlorinated hydrocarbon and water, to form a solution having a concentration of ethylcellulose of 0.5–4% by weight based on the total weight of the solution, and spray-drying the solution by introducing said solution into a spray dryer at an inlet temperature for the spray dryer of higher than 50° C., to obtain spherical, hollow particulates having a diameter of about 10–200 μ, an internal space volume ratio of greater than about 50%, and an apparent density of less than about 0.7.

2. A process for preparing a shperical particulate material composed of a shell of ethylcellulose completely surrounding a pharmacologically active ingredient, which comprises dissolving ethylcellulose in a solvent selected from the group consisting of a lower chlorinated hydrocarbon, a mixture of a lower chlorinated hydrocarbon and a lower chlorofluorinated hydrocarbon, a mixture of a lower chlorinated hydrocarbon, a lower chlorofluorinated hydrocarbon and water, and a mixture of a lower chlorinated hydrocarbon and water, to form a solution having a concentration of ethylcellulose of 0.5–4% by weight based on the total weight of the solution, mixing a pharmacologically active ingredient, and optionally a pharmaceutical excipient, with said solution, and spray-drying the resultant mixture by introducing said mixture into a spray dryer at an inlet temperature for the spray dryer of higher than 50° C., to obtain spherical, hollow particulates having a diameter of about 10–200 μ, an internal space volume ratio of greater than about 50%, and an apparent density of less than about 0.7.

3. A process as claimed in claim 2, wherein the solvent is a lower chlorinated hydrocarbon.

4. A process as claimed in claim 2, wherein the solvent is a mixture of a lower chlorinated hydrocarbon and a lower chlorofuorinated hydrocarbon.

5. A process as claimed in claim 2, wherein the solvent is a mixture of a lower chlorinated hydrocarbon, a lower chlorofluorinated hydrocarbon and water.

6. A process as claimed in claim 2, wherein the solvent is a mixture of a lower chlorinated hydrocarbon and water.

7. A process as claimed in claim 2, wherein the pharmacologically active ingredient is a medicine which effects the gastric mucous membrane.

8. A process as claimed in claim 2, wherein the pharmacologically active ingredient is a medicine which is absorbed by the gastric mucous membrane to exhibit its medicinal effects.

9. A process as claimed in claim 2, wherein the pharmacologically active ingredient is a medicine which effects the gastric juice.

10. A process as claimed in claim 2, wherein the pharmacologically active ingredient is an antacid.

11. A process as claimed in claim 2, wherein the pharmacologically active ingredient is an anti-pepsin agent.

12. A process as claimed in claim 2, wherein the pharmacologically active ingredient is local anesthetic accelerator of gastric motion.

13. A process as claimed in claim 2, wherein the pharmacologically active ingredient is benactyzine hydrochloride.

14. A process as claimed in claim 2, wherein the pharmacologically active ingredient is oxethazaine.

15. A process as claimed in claim 2, wherein the excipient is a precipitated calcium carbonate.

16. A process as claimed in claim 2, wherein the pharmacologically active ingredient is S-PI of the formula

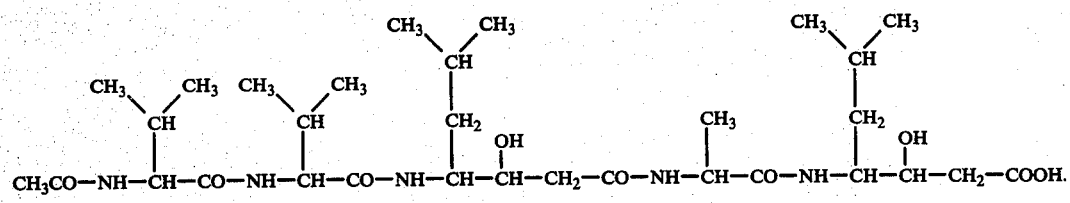

17. A process as claimed in claim 2, wherein the total weight amount of the pharmacologically active ingredient and, if present, the pharmaceutical excipient, is less than 8 times the weight of the ethylcellulose.

* * * * *